United States Patent [19]

Loiseau et al.

[11] 4,166,852
[45] Sep. 4, 1979

[54] PIPERAZINO-PYRIMIDINES AND THEIR USE AS SPASMOLYTIC AGENTS

[75] Inventors: Gerard P. M. H. Loiseau, Sceaux; Georges D. Mattioda, Enghien les Baines; Rene J. Millischer, Pringy; Pierre M. J. Obellianne, Paris, all of France

[73] Assignee: Produits Chimiques Ugine Kuhlmann, Courbevoie, France

[21] Appl. No.: 772,898

[22] Filed: Feb. 28, 1977

Related U.S. Application Data

[63] Continuation of Ser. No. 599,302, Jul. 25, 1975, abandoned, which is a continuation-in-part of Ser. No. 406,131, Oct. 12, 1973, abandoned.

[30] Foreign Application Priority Data

Aug. 9, 1974 [FR] France .................. 74 27671

[51] Int. Cl.$^2$ .................. A61K 31/505; C07D 403/04
[52] U.S. Cl. .................................... 424/251; 544/295; 544/298; 544/320; 544/332; 544/121
[58] Field of Search ................ 424/251; 260/256.5 R, 260/256.4 C, 256.4 R

[56] References Cited

U.S. PATENT DOCUMENTS

| | | | |
|---|---|---|---|
| 2,985,657 | 7/1967 | Janssen | 260/256.5 R |
| 3,060,183 | 10/1962 | Clark et al. | 260/256.5 R |
| 3,299,067 | 1/1967 | Regnier et al. | 260/256.5 R |
| 3,585,193 | 6/1971 | Regnier | 260/256.5 R |
| 3,843,656 | 10/1974 | Obellaine | 260/256.5 R |

*Primary Examiner*—Leonard Schenkman
*Attorney, Agent, or Firm*—Beveridge, DeGrandi, Kline & Lunsford

[57] ABSTRACT

The compounds of the formula:

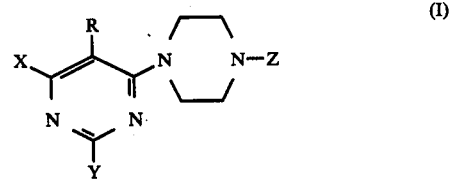

in which R represents a methyl or methylthio group, X represents a halogen atom or an alkoxy group containing 1 to 5 carbon atoms, Y represents an acylamino group or a substituted or unsubstituted amino group, Z represents a hydrogen atom or a methyl, ethyl, hydroxyethyl or phenyl group, with the exception of 2-methylamino-4-N-methylpiperazino-5-methylthio-6-chloro-pyrimidine; process for their preparation: medicaments comprising such compounds or salts thereof and with pharmaceutically acceptable acids and the use of such compounds or salts in the treatment of human beings.

19 Claims, No Drawings

PIPERAZINO-PYRIMIDINES AND THEIR USE AS SPASMOLYTIC AGENTS

CROSS-REFERENCES TO RELATED APPLICATIONS

This application is a continuation of application Ser. No. 599,302, filed July 25, 1975, now abandoned, which in turn is a continuation-in-part of application Ser. No. 406,131 filed Oct. 12, 1973, now abandoned.

BACKGROUND OF THE INVENTION

The present invention concerns piperazino-pyrimidines, process for their preparation and their use.

United Kingdom Patent Application No. 9975/73 describes 2-methylamino-4-N-methylpiperazino-5-methylthio-6-chloropyrimidine, a process for its preparation, and its action on the central nervous system.

SUMMARY OF THE INVENTION

According to the present invention compounds are provided of the general formula:

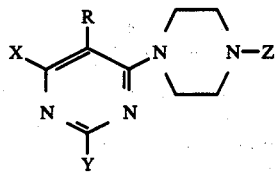

(I)

in which R represents a methyl or methylthio group, X represents a halogen atom or an alkoxy group containing 1 to 5 carbon atoms, Y represents an acylamino group or a substituted or unsubstituted amino group, Z represents a hydrogen atom or a methyl, ethyl, hydroxyethyl or phenyl group, with the exception of 2-methylamino-4-N-methylpiperazino-5-methylthio-6-chloro-pyrimidine.

DETAILED DESCRIPTION

Substituted amino groups which may be mentioned are especially the alkylamino groups containing 1 to 4 carbon atoms, for example, the methyl amino, ethylamino or isopropylamino groups, arylamino groups, for example phenylamino, N-alkyl-N-phenylamino, and heterocyclic radicals in which the hetero-atom is nitrogen for example, the morpholino, piperidino, piperazino or 4-methyl-piperazino groups.

Included within the invention are compounds of the general formula:

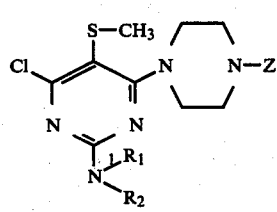

(II)

wherein Z represents an alkyl group having 1 to 4 carbon atoms, $R_1$ represents a hydrogen atom or a methyl or ethyl group, and $R_2$ represents a linear alkyl group having 3 to 6 carbon atoms, an allyl, hydroxyethyl or cycloalkyl group having 3 to 8 carbon atoms, a benzyl or p-methoxyphenyl group, and the —$NR_1R_2$ residue may represent a morpholino group.

The compounds of formula (I) in which R represents a methylthio group and X represents a chlorine atom are particularly advantageous.

The compounds of the invention of formula (I) may be prepared for example by reacting a 4,6-dichloropyrimidine of the formula:

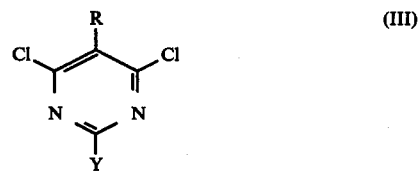

(III)

with a piperazine of the formula:

(IV)

in an anhydrous medium, in the presence of an acid-absorbing agent, at a temperature between 40° C. and 120° C. and possibly replacing the chlorine atom of the product obtained of the formula:

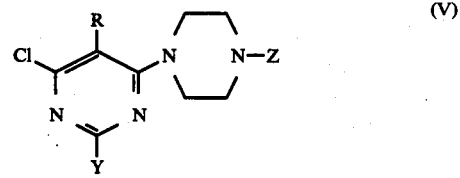

(V)

by an alkoxy group containing 1 to 5 carbon atoms.

This conversion may be effected for example by the action of a sodium alcoholate in dimethyl sulphoxide medium at a temperature approaching 100° C. or by the action of an excess of the corresponding alcohol and caustic potash at reflux temperature.

The compounds of formula (III), in which Y represents a mono- or di-substituted amino group or a nitrogen heterocyclic radical, may be prepared for example by reacting 2,4,6-trichloropyrimidine of the formula:

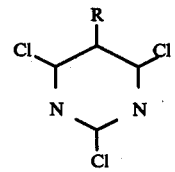

with the corresponding amine. The separation of the isomers formed may be facilitated by operating in a water-methylethylketone mixture. They may also be separated during the later substitution.

In the case where Y is a non-substituted or mono-substituted amino group, it is possible to acylate by any of the known processes, for example, by the action of an acid anhydride or by the action of an acid chloride in aqueous or anhydrous medium. This acylation may be effected on the 2-amino-4-piperazine-pyrimidine or before the chlorination of the intermediate pyrimidine-4,6-dione.

The compounds of formula (II) may be prepared for example by the process described above using the corresponding

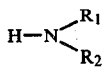

amines.

The products according to the invention have interesting pharmaceutical properties.

In the following Examples, which are purely illustrative, the parts are parts by weight unless the contrary is stated.

EXAMPLE 1

2-Ethylamino-4-N-methyl-piperazino-6-chloro-5-methylthio-pyrimidine hydrochloride (a) 2-Ethylamino-4,6-dichloro-5-methylthio-pyrimidine 230 parts of 2,4,6-trichloro-5-methylthio-pyrimidine are dissolved in 740 parts of methylethylketone, 650 parts of ice are added, and 120 parts of an aqueous 38% solution of ethylamine are run in over 30 minutes while cooling in order that the temperature should not exceed 5° C. 129.5 parts of a 31% solution of caustic soda are added in a period of an hour at 20° C. and the mixture is stirred for 6 hours. The desired isomer is then precipitated while the 4-ethylamino-2,6-dichloro-5-methylthiopyrimidine remains in solution. After cooling for 15 hours, the product is filtered off and washed with methylethylketone. 73 parts of the desired product are obtained, which is recrystallised from ethanol. M.p. 147° C.

(b) 2-Ethylamino-4-N-methylpiperazino-6-chloro-5-methylthiopyrimidine 31.4 parts of the product obtained in (a) are dissolved in 650 parts by volume of ethanol while heating to 70° C. 40 parts of N-methylpiperazine are run in over 10 minutes. The mixture is maintained under reflux for 3 hours and is then cooled to −40° C. and the product filtered off and washed with water. 29 parts of the desired product are obtained, which is recrystallised from ethanol. M.p. 101° C. The hydrochloride is obtained by the action of the calculated amount of hydrochloric acid in an ethanol medium.

| Analysis: | C | H | N | Cl |
|---|---|---|---|---|
| Calculated % | 41.06 | 6.38 | 19.96 | 20.24 |
| Found % | 41.18 | 6.30 | 19.60 | 20.07 |

EXAMPLE 2

2-Isopropylamino-4-N-methyl-piperazino-6-chloro-5-methylthio-pyrimidine (a) 2(4),6-Dichloro-4(2)-isopropylamino-5-methylthiopyrimidine The operation is as in Example 1, but the ethylamine is replaced by a corresponding amount of isopropylamine; the two isomers formed are isolated in an oily form. This mixture comprises about 40% of the desired isomer.

(b) 2-Isopropylamino-4-N-methylpiperazino-6-chloro-5-methylthio-pyrimidine 156 parts of the mixture of the two isomers obtained in (a) are heated under reflux for 3 hours with 180 parts of N-methyl-piperazine in 1200 parts of alcohol and then concentrated under vacuum. The residue is taken up in ether (500 parts) and separated by filtration. Only the desired isomer is insoluble under these conditions. It is separated from the hydrochloride of N-methylpiperazine by washing with water. 62 parts of the desired product are obtained, which is recrystallised from ethanol (M.p.: 145°–146° C.).

| | Molecular Weight 315.5 | | | | |
|---|---|---|---|---|---|
| Analysis for $C_{13}H_{22}N_5ClS$ | C | H | N | Cl | S |
| Calculated % | 49.44 | 6.97 | 22.18 | 11.25 | 10.14 |
| Found % | 49.46 | 6.97 | 22.16 | 11.33 | 10.14 |

EXAMPLE 3

2-t-butylamino-4-N-methylpiperazino-5-methylthio-6-chloro-pyrimidine

The procedure is as in Example 2, but t-butylamine is used instead of isopropylamine. The desired product crystallises from ethanol. M.p. 157° C.

| | Molecular weight 329.5 | | |
|---|---|---|---|
| Analysis for $C_{14}H_{24}N_5ClS$ | C | H | N |
| Calculated % | 50.98 | 7.28 | 21.24 |
| Found % | 50.82 | 7.27 | 21.19 |

EXAMPLE 4

2-phenylamino-4-N-methylpiperazino-6-chloro-5-methylthio-pyrimidine hydrochloride The procedure is as in Example 1, but aniline is used instead of ethylamine. The hydrochloride of 2-phenylamino-4-N-methylpiperazino-6-chloro-5-methylthio-pyrimidine is obtained.

| | Molecular weight 386 | | | |
|---|---|---|---|---|
| Analysis for $C_{16}H_{21}N_5SCl$ | C | H | N | Cl |
| Calculated % | 49.74 | 5.44 | 18.13 | 18.39 |
| Found % | 49.85 | 5.89 | 17.96 | 18.49 |

EXAMPLE 5

3′-Methoxy-2-propylamino-4-N-methylpiperazino-6-chloro-5-methylthio-pyrimidine

The procedure is as in Example 1, but 3′-methoxypropylamine is used instead of ethylamine. After distillation of the methylethylketone, a mixture of the two isomers of 3′-methoxy-2(4)-propylamino-4(2),6-dichloro-5-methylthio-pyrimidine is obtained containing 25% of the desired product.

The unwanted isomer is separated by dissolving the distillation residue (1 part) in concentrated hydrochloric acid d=1.19 (5 parts by volume) and diluting with water (2.2 parts). Under these conditions the 3′- methoxy-2-propylamino-4,6-dichloro-5-methylthio-pyrimidine is precipitated while the other isomer remains in solution: M.p. 85° C.

40 parts of 3'-methoxy-2-propylamino-4,6-dichloro-5-methylthio-pyrimidine in solution in 400 parts by volume of anhydrous ethanol and 43 parts of N-methylpiperazine are boiled under reflux for 3 hours. The ethanol is distilled off in vacuo, and the distillation residue is taken up in 300 parts by volume of ether. The N-methylpiperazine hydrochloride which precipitates is eliminated by filtration. The precipitate is washed on the filter with 300 parts by volume of ether. The filtrate is washed by decantation. After distilling off the ether, the residue, at first oily, crystallises. It is recrystallised from hexane and 40 parts of 3'-methoxy-2-propylamino-4-N-methylpiperazino-6-chloro-5-methylthiopyrimidine are obtained. M.p. 80° C.

| Analysis for $C_{14}H_{24}ON_5ClS$ | Molecular weight 345.5 | | | |
|---|---|---|---|---|
| | C | H | N | Cl |
| Calculated % | 48.62 | 6.94 | 20.26 | 10.27 |
| Found % | 48.62 | 7.34 | 20.11 | 10.48 |

EXAMPLE 6

2-Amino-4-N-methylpiperazino-6-chloro-5-methylthio-pyrimidine hydrochloride

In the same way as in Example 1, but replacing the ethylamine by ammonia, 2-amino-4-N-methylpiperazino-6-chloro-5-methylthio-pyrimidine is prepared. M.p. 191°–192° C. (ethanol).

| Analysis of the monohydrochloride (mol.wt. 310) $C_{10}H_{17}N_5SCl_2$ | | | | | |
|---|---|---|---|---|---|
| | C | H | N | Cl | S |
| Calculated % | 38.71 | 5.48 | 22.58 | 22.90 | 10.32 |
| Found % | 38.83 | 5.47 | 22.27 | 23.49 | 10.67 |

EXAMPLE 7

4-N-phenylpiperazino-2-methylamino-6-chloro-5-methylthio-pyrimidine

The 4-N-phenylpiperazino-2-methylamino-6-chloro-5-methylthio-pyrimidine, m.p. 163°–164° C., is prepared in the same way as in Example 1, but by the action of N-phenyl-piperazine on 2-methylamino-4,6-dichloro-5-methylthio-pyrimidine.

| Analysis for $C_{16}H_{20}N_5SCl$ | Molecular weight 349.5 | | | | |
|---|---|---|---|---|---|
| | C | H | N | Cl | S |
| Calculated % | 54.93 | 5.72 | 20.02 | 10.15 | 9.15 |
| Found % | 54.86 | 5.90 | 20.00 | 10.54 | 9.36 |

EXAMPLE 8

2-Methylamino-4-N-(β-hydroxyethyl)-piperazino-6-chloro-5-methylthio-pyrimidine

2-Methylamino-4-N(β-hydroxyethyl)-piperazino-6-chloro-5-methylthio-pyrimidine, m.p. 120°–122° C. (ethanol) is prepared in the same way as in Example 7, but using N-(β-hydroxyethyl)-piperazine instead of N-phenyl-piperazine.

| Analysis for $C_{12}H_{20}H_5OSCl$ | Molecular weight 317.5 | | | |
|---|---|---|---|---|
| | C | H | N | S |
| Calculated % | 45.35 | 6.30 | 22.04 | 10.08 |
| Found % | 45.21 | 6.28 | 21.83 | 10.58 |

EXAMPLE 9

Bis-2,4-(N-methylpiperazino)-6-chloro-5-methylthio-pyrimidine hydrochloride

The mixture of 2,4,6-trichloro-5-methylthio-pyrimidine with an excess of N-methylpiperazine is heated for 3 hours under reflux. Bis-2,4-(N-methylpiperazino)-6-chloro-5-methylthiopyrimidine is obtained, the hydrochloride of which has a M.p. >250° C. (decomp.).

| Analysis for $C_{15}H_{27}N_6SCl_3$, $H_2O$ | Molecular weight 489.5 | | | | |
|---|---|---|---|---|---|
| | C | H | N | Cl | S |
| Calculated % | 39.72 | 6.47 | 18.53 | 23.50 | 7.06 |
| Found % | 40.34 | 6.34 | 19.15 | 22.90 | 6.60 |

EXAMPLE 10

2-Methylamino-4-piperazino-6-chloro-5-methylthio-pyrimidine hydrochloride

The desired product, m.p. >250° C. (decomp.) is obtained by the action of anhydrous piperazine on 2-methylamino-4,6-dichloro-5-methylthio-pyrimidine under the conditions of Example 1.

| Analysis for $C_{10}H_{17}N_5SCl_2$ | Molecular weight 310 | | | | |
|---|---|---|---|---|---|
| | C | H | N | Cl | S |
| Calculated % | 38.71 | 5.48 | 22.58 | 22.90 | 10.32 |
| Found % | 38.88 | 5.56 | 22.44 | 22.94 | 10.88 |

EXAMPLE 11

2-Piperidino-4-methylpiperazino-5-methylthio-6-chloro-pyrimidine hydrochloride

The procedure is as in Example 1, but piperidine is used instead of ethylamine. The desired product is recrystallised from ethanol. M.p. 215° C. (decomp.).

| Analysis for $C_{15}H_{24}N_5SCl$, HCl | Molecular weight 378.4 | | | |
|---|---|---|---|---|
| | C | H | N | S |
| Calculated % | 47.60 | 6.65 | 18.50 | 8.45 |
| Found % | 47.60 | 7.01 | 18.65 | 8.45 |

EXAMPLE 12

2-(N-methyl-N-phenyl)amino-4-N-methylpiperazino-5-methylthio-6-chloro-pyrimidine hydrochloride The procedure is as in Example 1, but N-methylaniline is used instead of ethylamine. The desired product is recrystallised from ethanol. M.p. 220° C. (decomp.).

| Analysis for $C_{17}H_{22}N_5ClS$ HCl | Molecular weight 400.4 | | | |
|---|---|---|---|---|
| | C | H | N | S |
| Calculated % | 51.0 | 5.75 | 17.50 | 8.0 |

-continued

| Analysis for $C_{17}H_{22}N_5ClS$ HCl | Molecular weight 400.4 | | | |
|---|---|---|---|---|
| | C | H | N | S |
| Found % | 50.9 | 6.04 | 17.35 | 8.0 |

EXAMPLE 13

2-(N-methyl-N-benzoyl)amino-4-N-methyl-piperazino-6-chloro-5-methylthio-pyrimidine hydrochloride

28 parts of 2-N-methylamino-4-N-methylpiperazino-6-chloro-5-methylthio-pyrimidine in solution in 150 parts by volume of tetrahydrofuran are mixed with 10.5 parts of triethylamine. 13.7 parts of benzoyl chloride are run in over 30 minutes at the ambient temperature, then the mixture is heated under reflux for 5 hours. The triethylamine hydrochloride formed is separated, the filtrate is diluted with water and extracted with ether. The ethereal solution is washed with water, then dried over sodium sulphate and evaporated in vacuo. The residue is taken up a second time in ether so as to separate a little of the starting product. The monohydrochloride is formed in ethereal solution. M.p. ~210° C. It is recrystallised from ethanol.

| Analysis for $C_{18}H_{22}N_5ClSO$, HCl | Molecular weight 428.4 | | |
|---|---|---|---|
| | C | H | N |
| Calculated % | 50.46 | 5.41 | 16.34 |
| Found % | 50.20 | 5.33 | 15.93 |

EXAMPLE 14

2-Acetylamino-4-N-methylpiperazino-5-methyl-6-chloro-pyrimidine

(a) 2-Acetylamino-4,6-dioxo-5-methyl-pyrimidine 80 parts of 2-amino-4,6-dioxo-5-methyl-pyrimidine are treated for 8 hours under reflux in a mixture comprising 500 parts by volume of acetic acid and 108 parts by volume of acetic anhydride. 87 parts of the desired product are obtained by filtration, washing with ether and drying in vacuo.

(b) 2-Acetylamino-4,6-dichloro-5-methyl-pyrimidine 108 parts of phosphorus oxychloride are gradually introduced while maintaining the temperature at 0° C. into a mixture comprising 38 parts of 2-acetylamino-4,6-dichloro-5-methyl-pyrimidine and 46.5 parts of triethylamine in 255 parts of tetrahydrofuran. After stirring for 6 hours at the ambient temperature, the reaction mixture is poured into iced water and extracted with chloroform. The chloroform phase is washed with water, dried over sodium sulphate and concentrated to dryness. The residual solid is triturated in absolute ethanol, filtered and dried in vacuo.

| Analysis for $C_7H_7N_3Cl_2O$ | C | H | N | Cl |
|---|---|---|---|---|
| Calculated % | 38.20 | 3.20 | 19.10 | 32.30 |
| Found % | 38.60 | 3.70 | 19.05 | 32.0 |

(c) 2-Acetylamino-4-N-methylpiperazino-5-methyl-6-chloro-pyrimidine 8.8 parts of 2-acetylamino-4,6-dichloro-5-methyl-pyrimidine are dissolved in 100 parts by volume of tetrahydrofuran in the presence of 4 parts of triethylamine and 4 parts of N-methylpiperazine. The mixture is held for 6 hours at the reflux temperature. The reaction mixture is poured into water and the insoluble material is filtered off which is recrystallised from ethanol. M.p. 202° C.

| Analysis for $C_{12}H_{18}N_5OCl$ | C | H | H | Cl |
|---|---|---|---|---|
| Calculated | 50.80 | 6.39 | 24.70 | 12.50 |
| Found % | 50.52 | 6.53 | 24.64 | 12.20 |

EXAMPLE 15

2-N-diethylamino-4-N-methylpiperazino-5-methylthio-6-chloro-pyrimidine dihydrobromide

The procedure is as in Example 1, but diethylamine is used instead of ethylamine. The desired product is isolated in the form of the dihydrobromide. It is recrystallised from ethanol. M.p. 248° C. (decomp.).

| Analysis for $C_{14}H_{26}N_5OSClBr_2$ | Molecular weight 509.8 | | | |
|---|---|---|---|---|
| | C | H | N | Br |
| Calculated % | 32.97 | 5.14 | 13.73 | 31.35 |
| Found % | 32.65 | 5.26 | 14.08 | 31.90 |

EXAMPLE 16

2-(N-methyl-N-acetyl)amino-4-N-methylpiperazino-5-methylthio-6-chloro-pyrimidine hydrochloride

20 parts of 2-methylamino-4-N-methylpiperazino-5-methylthio-6-chloro-pyrimidine are held at the reflux temperature in 60 parts of acetic anhydride for 2 hours. The product is completely dissolved. After elimination of the excess of reagent the residue is treated with a dilute solution of caustic soda. The oil which separates is extracted with chloroform. The solvent is removed under vacuum. A white solid is obtained which is dissolved in ethanol in which the monohydrochloride is formed. This is recrystallised in an acetone/ethanol mixture. M.p. 188° C.

| Analysis for $C_{13}H_{20}N_5OSCl$, HCl | Molecular weight 366.3 | | | |
|---|---|---|---|---|
| | C | H | N | S |
| Calculated % | 42.65 | 5.77 | 19.22 | 8.75 |
| Found % | 42.90 | 5.75 | 18.90 | 8.35 |

EXAMPLE 17

2-Methylamino-4-N-methylpiperazino-5-methyl-thio-6-methoxy-pyrimidine hydrochloride

32 parts of 2-methylamino-4-N-methylpiperazino-5-methylthio-6-chloro-pyrimidine are dissolved in 100 parts by volume of dimethyl sulphoxide in the presence of 5.4 parts of sodium methylate. The temperature is held at 100° C., for 8 hours. The product is diluted with water, extracted with chloroform, the solvent is driven off and the hydrochloride is formed in absolute alcohol. 21 parts of product are obtained which is recrystallised from ethanol. M.p. 245° C. (decomp.).

| Analysis for $C_{12}H_{21}N_5OS$, HCl | Molecular weight 319.9 | | | |
|---|---|---|---|---|
| | C | H | N | Cl(Cl-) |
| Calculated % | 45.10 | 6.93 | 21.90 | 11.10 |
| Found % | 44.86 | 6.52 | 21.80 | 11.0 |

EXAMPLE 18

2-Methylamino-4-N-methylpiperazino-5-methylthio-6-propoxy-pyrimidine hydrochloride 20 parts of 2-methylamino-4-N-methylpiperazino-5-methylthio-6-chloro-pyrimidine are dissolved in 130 parts by volume of n-propanol in the presence of 7 parts of caustic potash in pellets. The mixture is held for 2 hours at the reflux temperature, then poured into water. The oil which separates is extracted with ether. The organic phase is washed with water, dried and evaporated. The residue is taken up in petrol ether in which it solidifies. It is recrystallised from the petrol ether. M.p. 90° C.

| Analysis for $C_{14}H_{25}N_5OS$ | Molecular weight 311.5 | | | |
|---|---|---|---|---|
| | C | H | N | S |
| Calculated % | 53.98 | 8.09 | 22.48 | 10.29 |
| Found % | 53.90 | 8.35 | 22.44 | 10.17 |

EXAMPLE 19

2-methylamino-4-N-methylpiperazino-5-methylthio-6-allyloxy-pyrimidine hydrochloride The hydrochloride indicated above is obtained in the same way as in Example 18 but allyl alcohol is used instead of n-propanol. M.p. 174° C. (decomp.).

| Analysis for $C_{14}H_{24}N_5SOCl$ | Molecular weight 345.9 | | | |
|---|---|---|---|---|
| | C | H | N | Cl |
| Calculated % | 48.61 | 6.99 | 20.24 | 10.24 |
| Found % | 48.32 | 7.11 | 20.36 | 9.90 |

EXAMPLE 20

2-Methylamino-4-N-methylpiperazino-5-methylthio-6-β-ethoxyethoxy-pyrimidine hydrochloride The procedure is as in Example 18, but β-ethoxyethanol is used instead of n-propanol. The hydrochloride indicated above is obtained. M.p. 136° C.

| Analysis for $C_{15}H_{27}N_5O_2S$, HCl | Molecular weight 378 | | | |
|---|---|---|---|---|
| | C | H | N | Cl |
| Calculated % | 47.70 | 7.16 | 18.52 | 8.46 |
| Found % | 47.98 | 7.25 | 18.62 | 8.60 |

The compounds described in the following Examples 21–32 have been prepared as in Example 1 but the ethylamine has been replaced by an equimolar quantity of the corresponding

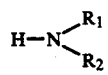

amine and the N-methylpiperazine has, where necessary, been replaced by an equimolar quantity of the corresponding N-alkyl-piperazine.

EXAMPLE 21

2-Allylamino-4-N-methylpiperazino-6-chloro-5-methylthio-pyrimidine

This water-insoluble product is in the form of a colourless crystalline powder which is soluble in alcohol and in dilute hydrochloric acid. MP: 89°–90° C. (Maquenne).

| Analysis: | C | H | N | Cl | S |
|---|---|---|---|---|---|
| Calculated % | 49.76 | 6.37 | 22.32 | 11.32 | 10.27 |
| Found % | 49.73 | 6.35 | 22.30 | 11.10 | 10.20 |

EXAMPLE 22

2-N-(β-hydroxyethyl)amino-4-N-methylpiperazino-6-chloro-5-methylthiopyrimidine Colourless crystals, insoluble in water, soluble in ethanol and in dilute hydrochloric acid. MP: 142° C. (Maquenne).

| Analysis: | C | H | N | Cl | S |
|---|---|---|---|---|---|
| Calculated % | 45.35 | 6.3 | 22.04 | 11.18 | 10.08 |
| Found % | 45.34 | 6.80 | 22.25 | 11.33 | 10.15 |

EXAMPLE 23

2-Cyclohexylamino-4-N-methylpiperazino-6-chloro-5-methylthiopyrimidine

Colourless crystalline powder, insoluble in water, soluble in ethanol and in dilute hydrochloric acid. MP: 129° C. (Köfler).

| Analysis: | C | H | N | Cl | S |
|---|---|---|---|---|---|
| Calculated % | 54.00 | 7.31 | 19.69 | 10.00 | 9.00 |
| Found % | 54.27 | 7.16 | 19.90 | 9.80 | 8.99 |

EXAMPLE 24

2-n-pentylamino-4-N-methylpiperazino-6-chloro-5-methylthiopyrimidine

Colourless crystalline powder, very soluble in ethanol, insoluble in water, soluble in dilute hydrochoric acid. MP: 60° C. (Köfler).

| Analysis: | C | H | N | Cl |
|---|---|---|---|---|
| Calculated % | 52.40 | 7.56 | 20.37 | 10.33 |
| Found % | 52.56 | 7.68 | 20.50 | 9.94 |

EXAMPLE 25

2-n-hexylamino-4-N-methylpiperazino-6-chloro-5-methylthiopyrimidine

Colourless crystalline powder, very soluble in solvents and in particular in ethanol, insoluble in water, soluble in dilute hydrochloric acid. MP:67° C. (Köfler).

| Analysis: | C | H | H | Cl |
|---|---|---|---|---|
| Calculated % | 53.76 | 7.83 | 19.58 | 9.94 |
| Found % | 53.79 | 7.58 | 19.93 | 9.89 |

EXAMPLE 26

2-Benzylamino-4-N-methylpiperazino-5-methylthio-6-chloropyrimidine

White crystalline product, soluble in water, scarcely soluble in dilute hydrochloric acid, soluble in dilute methanesulphonic acid. MP: 123° C. (Köfler).

| Analysis: | C | H | N |
|---|---|---|---|
| Calculated % | 56.12 | 6.05 | 19.26 |
| Found % | 56.08 | 5.99 | 19.33 |

EXAMPLE 27

2-(N-methyl N-benzylamino)-4-N-butylpiperazino-5-methylthio-6-chloropyrimidine hydrochloride White crystals, insoluble in water, soluble in dimethylsulphoxide. MP: 180° C. (Köfler).

| Analysis: | C | H | N |
|---|---|---|---|
| Calculated % | 55.25 | 6.84 | 15.34 |
| Found % | 55.25 | 6.48 | 15.21 |

EXAMPLE 28

2-Morpholino-4-N-methylpiperazino-6-chloro-5-methylthiopyrimidine

Colourless crystals, insoluble in water, soluble in ethanol, soluble in dilute hydrochloric acid. M.P.: 102° C.

| Analysis: | C | H | N | Cl | S |
|---|---|---|---|---|---|
| Calculated % | 48.90 | 6.40 | 20.37 | 10.33 | 9.31 |
| Found % | 49.07 | 6.71 | 20.83 | 10.40 | 9.65 |

EXAMPLE 29

2-Morpholino-4-N-butylpiperazino-5-methylthio-6-chloropyrimidine

White crystals, insoluble in water, soluble in ethanol and in a solution of dilute methanesulphonic acid. MP: 70° C.

| Analysis: | C | H | N |
|---|---|---|---|
| Calculated % | 52.90 | 7.31 | 18.15 |
| Found % | 52.95 | 7.36 | 18.39 |

EXAMPLE 30

2-n-propylamino-4-N-methylpiperazino-6-chloro-5-methylthiopyrimidine

Colourless crystalline powder, soluble in ethanol, insoluble in water, soluble in dilute hydrochloric acid. MP: 120° C. (Köfler).

| Analysis: | C | H | N | Cl |
|---|---|---|---|---|
| Calculated % | 49.44 | 6.97 | 22.18 | 11.25 |
| Found % | 49.51 | 6.77 | 22.45 | 11.22 |

EXAMPLE 31

2-n-butylamino-4-N-methylpiperazino-6-chloro-5-methylthiopyrimidine

Crystalline powder soluble in ethanol and dilute hydrochloric acid, insoluble in water. MP: 87° C. (Köfler).

| Analysis: | C | H | N | Cl |
|---|---|---|---|---|
| Calculated % | 50.98 | 7.28 | 21.24 | 10.77 |
| Found % | 51.10 | 7.22 | 21.40 | 10.37 |

EXAMPLE 32

4'-methoxy-2-phenylamino-4-N-methylpiperazino-6-chloro-5-methylthiopyrimidine Crystalline powder insoluble in water, soluble in dilute hydrochloric acid. MP: 144° C. (Köfler).

| Analysis: | C | H | N | Cl | S |
|---|---|---|---|---|---|
| Calculated % | 53.75 | 5.80 | 18.44 | 9.35 | 8.43 |
| Found % | 54.03 | 5.80 | 18.36 | 9.47 | 8.60 |

TOXICOLOGICAL PROPERTIES

The acute toxicities of the compounds according to the invention have been determined on CD 1 (Charles RIVER) mice by intravenous and oral methods. The LD 50 of each compound has been calculated by the cumulative method of J. J. Reed and H. Muench, (Amer. J. Hyg., 1938, 27, 493).

The LD 50 obtained are collected in the following Table:

| Product of Example | Acute toxicity for mice LD 50 mg/kg | |
|---|---|---|
| | Intravenous | orally |
| 1 | 41 | about 200 |
| 2 | 79 | about 525 |
| 3 | 67 | about 600 |
| 4 | insoluble | about 600 |
| 5 | 56 | about 200 |
| 6 | 33 | about 225 |
| 7 | — | atoxic 900 |
| 8 | 124 | about 525 |
| 9 | 83 | about 675 |
| 10 | 57 | about 225 |
| 11 | 115 | about 525 |
| 12 | 113 | about 525 |
| 13 | 91 | about 600 |
| 14 | insoluble | about 270 |
| 15 | 123 | about 600 |
| 16 | insoluble | about 525 |
| 17 | 58 | about 400 |
| 18 | 63 | about 525 |
| 19 | 56 | about 400 |
| 20 | insoluble | about 265 |
| 21 | 46 | about 200 |
| 22 | 89 | about 600 |
| 23 | 89 | above 900 |
| 24 | 87 | about 600 |
| 25 | 70 | above 900 |
| 26 | 85 | about 525 |

-continued

| Product of Example | Acute toxicity for mice LD 50 mg/kg | |
|---|---|---|
| | Intravenous | orally |
| 27 | insoluble | atoxic 900 |
| 28 | 110 | about 400 |
| 29 | insoluble | about 600 |
| 30 | 60 | about 200 |
| 31 | 98 | about 225 |
| 32 | 83 | about 495 |

The products according to the invention are not very toxic to mice either taken intravenously or orally since their LD 50 values are between 33 and 124 mg/kg intravenously and between 200 and more than 900 mg/kg orally.

PHARMACOLOGICAL PROPERTIES

1. Anti-emetic activity

The anti-emetic properties of the compounds according to the invention have been shown by oral administration of apomorphine to dogs in the vomiting test according to G. Chen and C. J. Ensor, Pharmacol. exp. Therap., 98, 24 (1950).

The results obtained are given in the following Table:

| Product of Example | Anti-emetic activity on dogs ED 50 mg/kg orally |
|---|---|
| 1 | 0.35 |
| 2 | 0.12 |
| 5 | 5 |
| 5 | 1.7 |
| 6 | 0.11 |
| 8 | 0.25 |
| 10 | 0.07 |
| 13 | 1.9 |
| 14 | 3.7 |
| 17 | 1.4 |
| 18 | 3.9 |
| 19 | 1.5 |
| 21 | 0.80 |
| 22 | 0.85 |
| 24 | 1.90 |
| 25 | 5 |
| 26 | about 2 |
| 27 | 1.50 |
| 28 | above 5 |
| 29 | above 5 |
| 30 | 0.16 |
| 31 | about 3 |

The compounds of Examples 10, 6, 2, 8 1 and 30 appear as the most strong anti-vomiting agents.

2. Neuroloptic activities

The neuroloptic effects of the compounds according to the invention have been shown with respect to the CD rat (Charles RIVER) taken orally in the catalepsy test according to S. COURVOISIER, R. DUCROT, and L. JULOU, in Psychotropic Drugs, S. GARATTINI and V. GHETTI, Edit.—ELSEVIER Publ. Co., AMSTERDAM, LONDON, NEW YORK, PRINCETON, 1957 P. 373 and also in the traction test of CD1 (Charles RIVER) mice taken orally S. COURVOISIER, Quart. Rev. Psychiat. Neurol. 17, 25 (1956), on the one hand and also in the spontaneous motility test.

This latter technique comprises keeping an account of the displacements of the mice by means of a floor of metal strips which enables the spontaneous activity of the animals to be recorded during the first 5 minutes subsequent to their being introduced into the measuring chamber. The products are dispensed 60 minutes before measuring is effected and 10 mice are used per dose. The results are expressed in ED 50 which represents the dose of substance capable of reducing the mean motility of the treated animals by 50% relative to that of the sample group which has only received the dispensing carrier.

The Table below gives the effects obtained with the compounds of Examples 1, 5, 6 and 10.

| Product of Examples | Rat Catalepsy AD 50 mg/kg orally | Mouse Traction AD 50 mg/kg orally |
|---|---|---|
| 1 | 85 | over 35 |
| 5 | 175 | 30 |
| 6 | 100 | over 100 |
| 10 | 75 | — |

The Table below gives the psycholeptic effects which have been obtained.

| Product of Example | Rat Catalepsy AD 50 (mg/kg) orally | Mouse Traction AD 50 (mg/kg) orally | Mouse Hypomotility ED 50 (mg/kg) orally |
|---|---|---|---|
| 21 | 300 | — | 28 |
| 22 | — | — | 100 |
| 23 | 300 | above 300 | 220 |
| 24 | 400 | 210 | 80 |
| 25 | above 300 | above 300 | 70 |
| 26 | 33 | 45 | 20 |
| 27 | — | — | 160 |
| 28 | — | — | 100 |
| 29 | — | — | 50 |
| 30 | above 300 | — | 25 |
| 31 | — | — | 20 |
| 32 | — | — | 60 |

The compound of Example 26 proves to be the most active.

3. Analgesic activity

The analgesic properties of the products according to the invention have been shown with CD 1 (Charles RIVER) mice in the painful abdominal torsions test with phenylbenzoquinone according to the technique of E. Siegmund, R. Cadmus and Go.Lu—Proc. Soc. Exp. Biol. Med., 95, 729, (1957).

The following Table tabulates the AD 50 obtained.

The compounds of Examples 5,1, 14 and 26 are the most active.

| Product of Examples | Phenylbenzoquinone test on mice AD 50 mg/kg orally |
|---|---|
| 1 | 35 |
| 2 | 65 |
| 5 | 35 |
| 9 | 150 |
| 10 | 65 |
| 12 | 100 |
| 14 | 35 |
| 15 | 300 |
| 19 | 100 |
| 21 | higher than 100 |
| 22 | higher than 100 |
| 23 | 100 |
| 24 | 100 |
| 25 | 85 |
| 26 | 35 |
| 27 | 400 |
| 28 | higher than 100 |
| 29 | 55 |
| 30 | higher than 400 |

| Product of Examples | Phenylbenzoquinone test on mice AD 50 mg/kg orally |
|---|---|
| 31 | 100 |
| 32 | higher than 35 |

4. Anti-serotonine activities

The anti-serotonine activities of the compounds according to the invention have been shown by oral administration to the CD (Charles RIVER) rats using the technique of the serotonine plantar oedema (W. Theobald and R. Domenjoz—Arzneimittel Forsch, 8, 18, 1958 and with the CD 1 (Charles RIVER) mice using the technique known as "head twitch" according to S. J. Corne, R. W. Pickering and B. T. Warner, Brit. J. Pharmacol., 20, 106, (1963). The anti-serotonine activity has also been determined on the one hand on the tricoloured guinea-pig, given intravenously, according to a method derived from H. Konzet and R. Rossler, Arch. exp. Pathol, Pharmakol., 195, 71, (1940) and on the other hand in vitro with respect to the serotonine spasm of the isolated uterus of the rat according to the technique of A. Fanchamps, W. Doepfener, H. Weidman and A. Cerletti, Schw. Med. Worsch, 90, 1940, (1960).

The following Table indicates the results obtained:

| Products of Ex. | Rat taken orally Serotonine plantar oedema AD 50 mg/kg | Mice taken orally "Head-twitch" AD 50 mg/kg | Guinea pig intravenously Serotonine broncho-spasms ED 50 mg/kg | Isolated uterus of rat Serotonine spasm EC 50 mg/kg |
|---|---|---|---|---|
| 1 | 160 | 30 | 6 | 0.05 |
| 3 | — | 300 | — | — |
| 4 | — | 60 | — | — |
| 5 | 90 | 35 | — | — |
| 6 | — | 30 | 1.2 | 0.05 |
| 7 | — | 400 | — | — |
| 9 | — | 300 | — | 0.6 |
| 12 | — | 100 | — | — |
| 13 | over 300 | 300 | — | — |
| 16 | 100 | over 100 | — | — |
| 17 | 100 | — | 3 | — |
| 19 | over 100 | 100 | — | — |
| 21 | higher than 100 | 20 | 0.01 | 0.02 |
| 22 | — | higher than 100 | 0.16 | 0.60 |
| 23 | — | 67 | 0.30 | 0.05 |
| 24 | higher than 300 | 25 | 0.05 | 0.05 |
| 25 | about 300 | 55 | 0.18 | 0.02 |
| 26 | — | 17 | 0.05 | 0.05 |
| 27 | higher —127 400 | — | — | — |
| 28 | higher than 100 | 70 | higher than 0.1 | 0.18 |
| 29 | — | 80 | — | — |
| 30 | — | 10 | 0.05 | 0.05 |
| 31 | higher than 100 | 13 | 0.10 | 0.01 |
| 32 | — | 27 | 0.90 | 0.13 |

The compounds of Examples 1,5,6, 30, 31, 21, 24 and 26 exhibit the greatest antiserotonine properties on the whole.

5. Spasmolytic activities

The spasmolytic properties of the compounds have been demonstrated by means of the technique of R. Magnus, Arch. Ges. Physiol., 102, 123, (1904) with respect to the spasms of the isolated duodenum of rabbits caused either by acetylchlorine for the spasmolytic nemotropes or by barium chloride for the spasmolytic musculotropes.

The results obtained are collected in the following Table:

| Products of Examples | Spasmolytic effects on the isolated duodenum of the rabbit (EC 50 mg/l) | |
|---|---|---|
| | with respect to acetylcholine | with respect to barium chloride |
| 1 | 5 | 1.6 |
| 2 | 5 | 1.2 |
| 3 | 2.5 | 0.5 |
| 5 | over 5 | 1.3 |
| 8 | 5 | 1.3 |
| 9 | over 10 | 3.6 |
| 11 | 2.5 | 2.2 |
| 12 | 3 | 2.2 |
| 13 | 4 | 2.6 |
| 15 | 5 | 4 |
| 18 | over 5 | 2.1 |
| 19 | over 5 | 3.1 |
| 21 | 1.60 | 1.00 |
| 22 | more than 10 | more than 10 |
| 23 | 70 | 0.25 |
| 24 | 0.50 | 0.12 |
| 25 | 1.00 | 0.20 |
| 26 | 0.20 | 0.17 |
| 28 | 4.50 | 1.70 |
| 30 | 9.00 | 0.20 |
| 31 | 1.20 | 0.30 |
| 32 | 5.50 | — |

The products according to the invention exert a spasmolytic activity essentially of the musculotropic type. The most effective ones are those of Examples 3, 2, 5, 8, 24, 26, 25, 23 and 30.

THERAPEUTIC UTILISATION

The products according to the invention and their pharmaceutically acceptable salts may be used in human therapeutics in the form for example of compressed tablets, lozenges, gelatine-coated pills, suppositories, ingestable or injectable solutions for the treatment of vomiting, nausea and migraines of all origins or digestive and other spasms. They may also be used as psychotropes, analgesics, anti-serotonines and spasmolytics.

They may be administered in the form for example of compressed tablets, lozenges, gelatine-coated pills, cachets, suppositories, injectable ampoules or drops in unit doses which comprise, according to the form and the compound used, between 10 mg and 500 mg, and according to a daily dose between 50 mg and 2500 mg.

We claim:

1. The compound: 2-isopropyl-amino-4-N-methyl piperazino-6-chloro-5-methylthio-pyrimidine.
2. The compound: 2-ethylamino-4-N-methyl-piperazino-6-chloro-5-methylthio-pyrimidine.
3. The compound: 2-t-butylamino-4-N-methyl-piperazino-6-chloro-5-methylthio-pyrimidine.
4. The compound: 2-(N-methyl-N-phenyl)amino-4-N-methylpiperazino-6-chloro-5-methylthio-pyrimidine.
5. The compound: 2-N-diethylamino-4-N-methyl-piperazino-6-chloro-5-methylthio-pyrimidine.
6. The compound: 2-allylamino-4-N-methyl-piperazino-6-chloro-5-methylthio-pyrimidine.
7. The compound: 2-cyclohexylamino-4-N-methyl-piperazino-6-chloro-5-methylthio-pyrimidine.

8. The compound: 2-n.pentylamino-4-N-methylpiperazino-6-chloro-5-methylthio-pyrimidine.

9. The compound: 2-n.hexylamino-4-N-methylpiperazino-6-chloro-5-methylthio-pyrimidine.

10. The compound: 2-benzylamino-4-N-methylpiperazino-6-chloro-5-methylthio-pyrimidine.

11. The compound: 2-n.propylamino-4-N-methylpiperazino-6-chloro-5-methylthio-pyrimidine.

12. The compound: 2-n.butylamino-4-N-methylpiperazino-6-chloro-5-methylthio-pyrimidine.

13. The compound: 2-methylamino-4-N-($\beta$-hydroxyethyl)piperazino-6-chloro-5-methylthio-pyrmidine.

14. The compound: 2-(N-methyl-N-benzoyl)amino-4-N-methylpiperazino-6-chloro-5-methylthio-pyrimidine.

15. A pharmaceutical composition in unit dosage form comprising 10 mg to 500 mg of a compound selected from the group consisting of:
2-isopropylamino-4-N-methylpiperazino-6-chloro-5-methylthio-pyrimidine;
2-ethylamino-4-N-methylpiperazino-6-chloro-5-methylthio-pyrimidine;
2-t-butylamino-4-N-methylpiperazino-6-chloro-5-methylthio-pyrimidine;
2-(N-methyl-N-phenyl)amino-4-N-methylpiperazino-6-chloro-5-methylthio-pyrimidine;
2-N-diethylamino-4-N-methylpiperazino-6-chloro-5-methylthio-pyrimidine;
2-allylamino-4-N-methylpiperazino-6-chloro-5-methylthio-pyrimidine;
2-cyclohexylamino-4-N-methylpiperazino-6-chloro-5-methylthio-pyrimidine;
2-n.pentylamino-4-N-methylpiperazino-6-chloro-5-methylthio-pyrimidine;
2-n.hexylamino-4-N-methylpiperazino-6-chloro-5-methylthio-pyrimidine;
2-benzylamino-4-N-methylpiperazino-6-chloro-5-methylthio-pyrmidine;
2-n.propylamino-4-N-methylpiperazino-6-chloro-5-methylthio-pyrimidine;
2-n.butylamino-4-N-methylpiperazino-6-chloro-5-methylthio-pyrimidine;
2-methylamino-4-N-($\beta$-hydroxyethyl)piperazino-6-chloro-5-methylthio-pyrimidine; and
2-(N-methyl-N-benzoyl)amino-4-N-methylpiperazino-6-chloro-5-methylthio-pyrimidine,
or a salt thereof with a pharmaceutically acceptable acid, and a pharmaceutically acceptable carrier.

16. Process for the treatment of spasms in a human being which comprises administering to a human in need thereof, as a spasmolytic agent, an effective amount of a compound selected from the group consisting of:
2-isopropylamino-4-N-methylpiperazino-6-chloro-5-methylthio-pyrimidine;
2-ethylamino-4-N-methylpiperazino-6-chloro-5-methylthio-pyrimidine;
2-t-butylamino-4-N-methylpiperazino-6-chloro-5-methylthio-pyrimidine;
2-(N-methyl-N-phenyl)amino-4-N-methylpiperazino-6-chloro-5-methylthio-pyrimidine;
2-N-diethylamino-4-N-methylpiperazino-6-chloro-5-methylthio-pyrimidine;
2-allylamino-4-N-methylpiperazino-6-chloro-5-methylthio-pyrimidine;
2-cyclohexylamino-4-N-methylpiperazino-6-chloro-5-methylthio-pyrimidine;
2-n.pentylamino-4-N-methylpiperazino-6-chloro-5-methylthio-pyrimidine;
2-n.hexylamino-4-N-methylpiperazino-6-chloro-5-methylthio-pyrimidine;
2-benzylamino-4-N-methylpiperazino-6-chloro-5-methylthio-pyrmidine;
2-n.propylamino-4-N-methylpiperazino-6-chloro-5-methylthio-pyrimidine;
2-n.butylamino-4-N-methylpiperazino-6-chloro-5-methylthio-pyrimidine;
2-methylamino-4-N-($\beta$-hydroxyethyl)piperazino-6-chloro-5-methylthio-pyrimidine; and
2-(N-methyl-N-benzoyl)amino-4-N-methylpiperazino-6-chloro-5-methylthio-pyrimidine,
or a salt thereof with a pharmaceutically acceptable acid, and a pharmaceutically acceptable carrier.

17. Process for the treatment of spasms in a human being which comprises orally or intravenously administering to a human in need thereof, as a spasmolytic agent of low toxicity, an effective amount of a compound selected from the group consisting of:
2-isopropylamino-4-N-methylpiperazino-6-chloro-5-methylthio-pyrimidine;
2-ethylamino-4-N-methylpiperazino-6-chloro-5-methylthio-pyrimidine;
2-t-butylamino-4-N-methylpiperazino-6-chloro-5-methylthio-pyrimidine;
2-(N-methyl-N-phenyl)amino-4-N-methylpiperazino-6-chloro-5-methylthio-pyrimidine;
2-N-diethylamino-4-N-methylpiperazino-6-chloro-5-methylthio-pyrimidine;
2-allylamino-4-N-methylpiperazino-6-chloro-5-methylthio-pyrimidine;
2-cyclohexylamino-4-N-methylpiperazino-6-chloro-5-methylthio-pyrimidine;
2-n.pentylamino-4-N-methylpiperazino-6-chloro-5-methylthio-pyrimidine;
2-n.hexylamino-4-N-methylpiperazino-6-chloro-5-methylthio-pyrimidine;
2-benzylamino-4-N-methylpiperazino-6-chloro-5-methylthio-pyrmidine;
2-benzylamino-4-N-methylpiperazino-6-chloro-5-methylthio-pyrimidine;
2-n.propylamino-4-N-methylpiperazino-6-chloro-5-methylthio-pyrimidine;
2-n.butylamino-4-N-methylpiperazino-6-chloro-5-methylthio-pyrimidine; and
2-methylamino-4-N-($\beta$-hydroxyethyl)piperazino-6-chloro-5-methylthio-pyrimidine,
or a salt thereof with a pharmaceutically acceptable acid at a daily dose of 50 mg to 2500 mg.

18. Process according to claim 17 wherein said compound is administered orally.

19. Process according to claim 17 wherein said compound is administered intravenously.

* * * * *